United States Patent [19]
Wu

[11] Patent Number: 6,127,688
[45] Date of Patent: Oct. 3, 2000

[54] ISO-ENERGETIC INTENSITY MODULATOR FOR THERAPEUTIC ELECTRON BEAMS, ELECTRON BEAM WEDGE AND FLATTENING FILTERS

[75] Inventor: Xiaodong Wu, Miami, Fla.

[73] Assignee: The University of Miami, Miami, Fla.

[21] Appl. No.: 09/020,004

[22] Filed: Feb. 6, 1998

[51] Int. Cl.$^7$ ........................................... H01J 37/09
[52] U.S. Cl. ................................ 250/505.1; 250/492.3
[58] Field of Search ........................... 250/505.1, 492.3; 378/149

[56] References Cited

U.S. PATENT DOCUMENTS

| | | | |
|---|---|---|---|
| 3,670,395 | 6/1972 | Abe et al. | 378/149 |
| 3,936,646 | 2/1976 | Jonker | 378/149 |
| 4,020,356 | 4/1977 | Brahme | 378/149 |
| 4,419,585 | 12/1983 | Strauss et al. | 250/505.1 |
| 5,012,506 | 4/1991 | Span et al. | 250/505.1 |
| 5,160,847 | 11/1992 | Leavitt | 250/505.1 |
| 5,177,361 | 1/1993 | Krahl | 250/305 |
| 5,468,970 | 11/1995 | Kocsis et al. | 250/505.1 |
| 5,479,469 | 12/1995 | Fraser et al. | 250/505.1 |
| 5,528,659 | 6/1996 | Stein | 378/149 |
| 5,621,270 | 4/1997 | Allen | 250/505.1 |
| 5,757,881 | 5/1998 | Hughs | 250/505.1 |

FOREIGN PATENT DOCUMENTS

| | | |
|---|---|---|
| 0 314 216 | 5/1989 | European Pat. Off. . |
| 2 137 802 | 10/1984 | United Kingdom . |

OTHER PUBLICATIONS

Patent Abstracts of Japan, vol. 013, No. 370 (P–920), Aug. 17, 1989 & JP 01 126600 A (Mitsubishi Electric Corp), May 18, 1989.
Database WPI, Section Ch, Week 9531; Derwent Publications Ltd., London, GB; Class L03, AN 95–237922 XP002065270 & JP 07 147 140 A (Mitsubishi Electric Corp).
Patent Abstracts of Japan, vol. 013, No. 175 (P–863), Apr. 25, 1989 & JP 01 009398 A (Mitsubishi Electric Corp), Jan. 12, 1989.
Patent Abstracts of Japan, vol. 014, No. 215 (C–0716), May 8, 1990 & JP 02 049670 A (Mitsubishi Electric Corp), Feb. 20, 1990.
Database WPI, Section Ch, Week 8922; Derwent Publications Ltd., London, GB; Class K08, AN 89–163750 XP00265269 & SU 1 437 929 A (MOSC Radiology X–RA).
Koh, et al., Current use of electron beam therapy in the United States, Radiologia medica. 80(4Suppl 1):26–7, Oct. 1990 (abstract only).
Kurup, et al., Field matching of electron beams using plastic wedge penumbra generators, Physics in Medicine & Biology. 37(1):145–53, Jan. 1992 (abstract only).
Kuttig et al., Electron therapy using wedge filters. I. Experimental studies using wedge filters made from polystyrol [German], Strahlentherapie. 150(4):383–8, Oct. 1975 (English abstract only).

(List continued on next page.)

*Primary Examiner*—Bruce C. Anderson
*Attorney, Agent, or Firm*—Pillsbury Madison & Sutro LLP

[57] ABSTRACT

This invention includes an iso-energetic intensity modulating filter and method for therapeutic charged-particle beams, preferably electron beams, in which attenuating members are arranged to completely attenuate portions of the beam while permitting other portions of the beam to pass through the space between attenuating members. The attenuating members block the charged particles without producing any significant bremsstrahlung contamination in the filtered beam. The attenuating members can be arranged in a large number of configurations to obtain the desired modulated beam intensity profile. This invention also includes an improved iso-energetic, intensity-modulated charged-particle beam produced by the filtering device and method of this invention. A charged-particle beam therapeutic device and treatment method which has the iso-energetic intensity modulating filter is also included in this invention.

29 Claims, 11 Drawing Sheets

OTHER PUBLICATIONS

Stiteler, et al., Electron field within an electron field treatment of the scalp or other curved surfaces., medical Dosimetry. 15(4):205–8, Dec. 1990 (abstract only).

Kalend, et al., A beam–edge modifier for abutting electron fields., medical Physics. 12(6):793–8, Nov.–Dec. 1985 (abstract only).

Das et al., Electron–beam characteristics at extended treatment distances., Medical Physics. 22(10):1667–74, Oct. 1995 (abstract only).

Leavitt, et al., Design and production of customized field shaping devices for electron arc therapy;, Medical Dosimetry. 15(1):25–31, Mar. 1990 (abstract only).

Mohan et al., The effect of angular spread on the intensity distribution of arbitrarily shaped electron beams., Medical Physics. 15(2):204–10, Mar.–Apr. 1988.

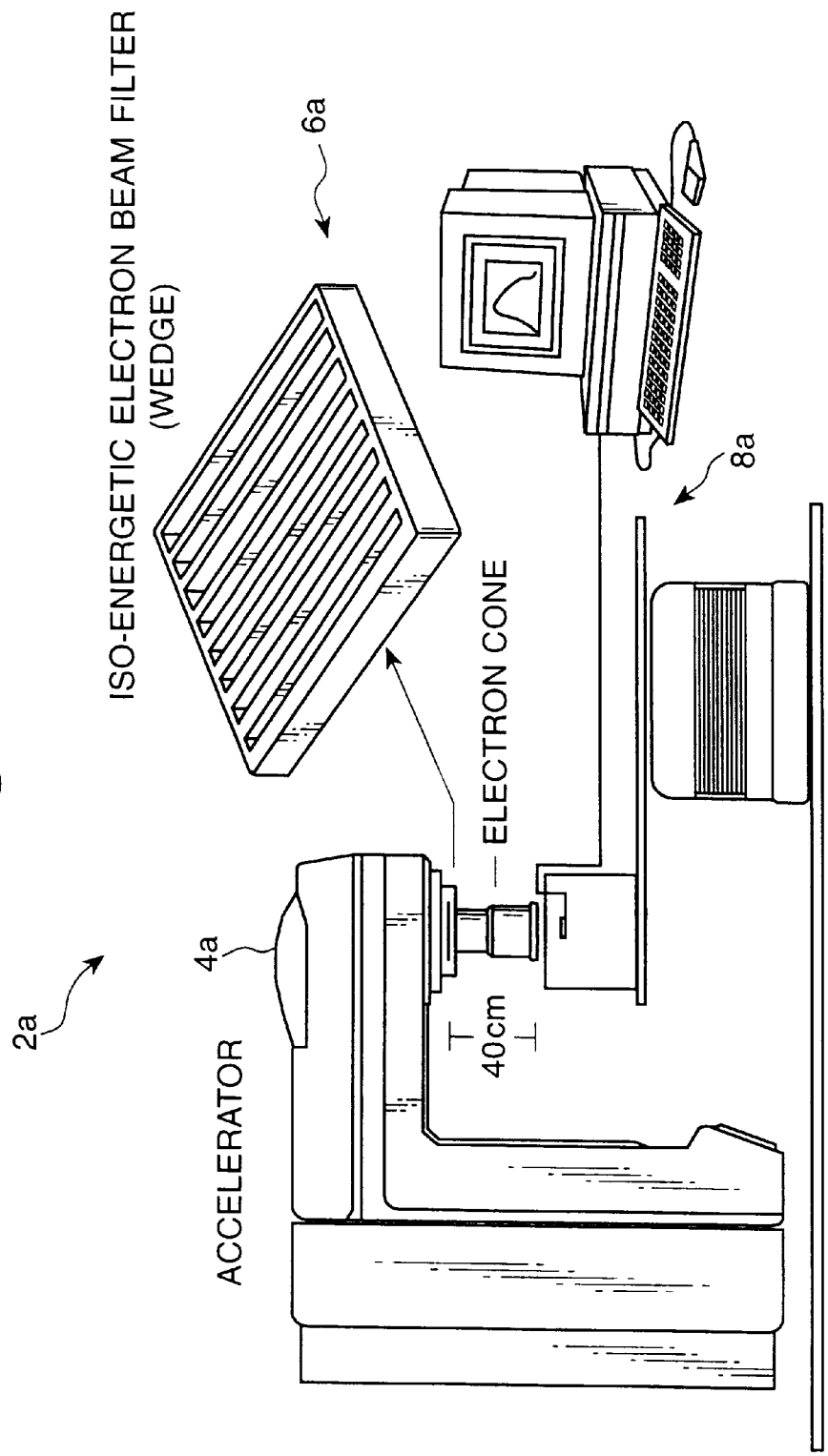

BROAD ELECTRON BEAM

ISO-ENERGETIC ELECTRON WEDGE

INTENSITY PROFILE foot　　　　　　　　　　　　　　　　　　　　　　　　head 1.5 cm

ISO-ENERGETIC INTENSITY MODULATOR FOR THERAPEUTIC ELECTRON BEAMS, ELECTRON BEAM WEDGE AND FLATTENING FILTERS

This application claims the benefit of priority based upon U.S. Provisional Application No. 60/037,390, filed on Feb. 7, 1997, the entire disclosure of which is hereby incorporated by reference.

BACKGROUND OF THE INVENTION

1. Field of the Invention

The field of this invention pertains to a device and method for isoenergetic intensity modulation of a beam of charged particles, and more particularly to a device and method for iso-energetic intensity modulation of a therapeutic electron beam.

2. Description of Related Art

High energy electron beams (MeV range) have been widely used in the field of radiotherapy. The principal applications for this type of radiotherapy are for skin cancer, chest well irradiation for breast cancer, administering boost doses to nodes, and the treatment of head and neck cancers (Faiz M. Khan, *The Physics of Radiation Therapy*, William & Wilkins).

Modern therapy linear accelerators provide electron beams with satisfactory field flatness and symmetry of the intensity profile. However, many clinical situations indicate that an electron beam with a tilted, concave, or asymmetric intensity profile is useful for the treatment of a curved or oblique skin surface.

Photon (gamma or x-ray) beams with a tilted beam intensity profile have become common practice and is achieved by placing a wedge shaped absorber (a commercially available standard accessory) in the photon beam path. While the same principle has been attempted in order to produce a tilted electron beam profile, the technique used for photon beams causes the electron beam energy to be seriously degraded throughout the modified electron field. Thus, heretofore there has been no commercially available electron wedge filter.

SUMMARY OF THE INVENTION

An object of this invention is to provide a device and method to modulate the intensity of a charged particle beam without substantially changing the energy of the charged-particle beam.

Another object of this invention is to provide a charged-particle therapeutic device which provides an intensity modulated charged-particle beam of substantially the same energy as the source beam.

Another object of the present invention is for a device and method to provide a desirable tilted (wedge, asymmetric) or concave (symmetric), or other shape of electron beam profile without substantially altering the original beam energy.

Another object of the present invention is to provide an improved isoenergetic intensity modulated charged-particle beam.

The principles of the present invention can be used to provide a single direct electron beam with adequate dose uniformity for total skin treatment.

When using the electron beam for total skin lesions, the patient is conventionally arranged at an extended distance from the radiation source (3 to 4 meters). The electron field at such extended distance will not provide adequate dose uniformity over a patient. The conventional treatment technique used to overcome this problem utilizes either a dual-field or triple-field configuration. The present invention provides a flattening filter to produce a large uniform electron beam profile without degrading the beam energy. Hence, the total skin electron beam treatment can be simplified by using a single direct beam.

BRIEF DESCRIPTION OF THE DRAWINGS

These and other objects and advantages of the invention will become more apparent and more readily appreciated from the following detailed description of the presently preferred exemplary embodiments of the invention taken in conjunction with the accompanying drawings, of which:

FIG. 1(a) is an illustration of an example of a charged-particle beam therapeutic device designed to produce iso-energetic intensity modulated beams according to this invention.

FIG. 3(a) further shows an incoming convex electron beam intensity profile and the flattened intensity profile of the electron beam output by the concentric ring filter, while FIG. 3(b) shows an incoming flat electron beam intensity profile and resulting concave electron beam intensity profile output by the concentric ring filter of the present invention.

DETAILED DESCRIPTION OF THE PREFERRED EMBODIMENTS

Due to the Coulomb multiple-scattering effect in an air medium, Gausian spread in air of the electron beam broadens with increasing distance from the linear accelerator source. Two parallel electron beams with limited separation will join together as one composite distribution at a certain distance from the source. Based on this physical principle, the intensity distribution of a broad electron beam can be modulated by dividing the broad beam into a plurality of narrow slit electron beams with different spatial separation. Since an intensity modulated electron beam results from the plurality of narrow electron beams which have the same energy characteristics (energy spectrum), the modulated beam will have the same energy as the original open beam. Although an electron beam is used in the preferred embodiments, this invention is not in limited to only electron beams. One skilled in the art would recognized that the teachings of this invention can be applied to charged particle beams, in general, since they exhibit Coulomb scattering off of the air molecules. However, the specification will refer to electron beams throughout since electron beams are preferred according to this invention. Unlike other electron beam modulation methods, this intensity modulation method is isoenergetic.

FIG. 1(a) illustrates an example of a charged-particle beam therapeutic device 2a according to this invention. The charged-particle beam therapeutic device 2a has a charged-particle beam source 4a, an iso-energetic intensity modulating filter 6a, and a patient positioning region 8a.

A first preferred embodiment of this invention is for an iso-energetic electron beam wedge filter.

Figure 1B:
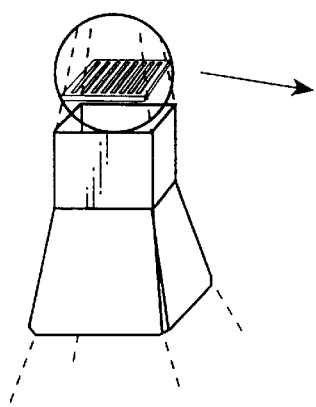
FIG. 1(b)–1(c) is a perspective view showing the parallel bar (also known as para-bar) electron wedge filter of the present invention used in conjunction with an electron beam collimator cone.
Figure 1C:
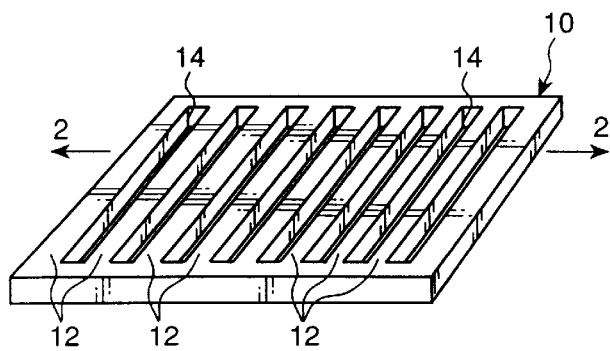

As shown in FIG. 1(b), the electron wedge filter of the present invention, indicated generally at 10, consists of a number of spaced high density metal bars 12 disposed in parallel side-by-side arrangement. Preferably the bars are metal bars. Each bar has a thickness and density sufficient to block the electron beam without producing any significant bremsstrahlung contamination. Preferably, the bars have a thickness of about 1.5 cm and are made from lead, tungsten, cerrobend, copper, steel, or iron. Most preferably, lead or tungsten is used. In any event, the same preferred metals are used for all embodiments of the present invention and preferably have a minimum density of 10 grams/cc.

Figure 2A:
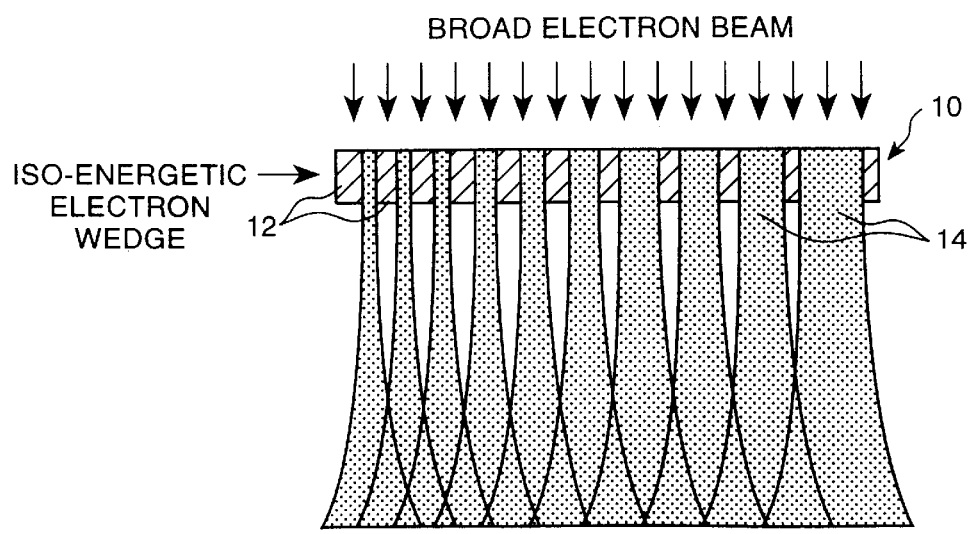
FIG. 2(a) is a cross-sectional view of the para-bar electron wedge of the present invention take through the line 2—2 in FIG. 1(b)

As shown in FIG. 2(a), the width and spacing between the bars 12 are varied to form a gradient of separation and openings. This configuration converts the broad beam into a plurality of narrow slit electron beams which emanate through the openings or spaces 14 between the parallel metal bars while the rest of the broad electron beam impinging upon the bars is blocked.

Figure 2B:
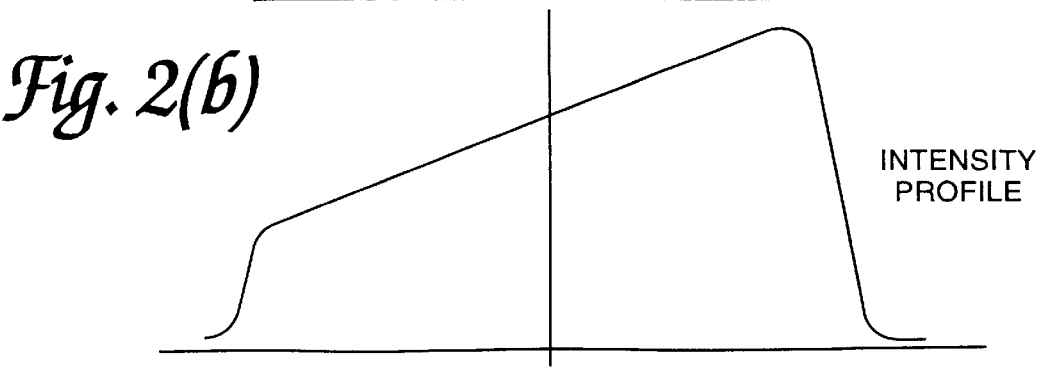
FIG. 2(b) shows the resulting electron beams and intensity distribution.

When in use, the wedge 10 is placed on top of an electron applicator at an adequate distance from the patient surface. The minimum distance between the wedge filter and patient required to produce a smooth profile depends on the spatial separation between each of the wedge filter bars and the electron beam energy. As the energy of the electron beam increases, a greater distance between the wedge and the surface of the patient is required to obtain a smooth intensity profile. Preferably, the minimum distance ranges from 15 cm to 40 cm for electron energies ranging from 6 MeV to 20 MeV. The electron wedge is preferably placed in the same slot in which photon wedges or other treatment modules such as total skin electron therapy (TSE) modules are usually placed. By doing so, the height of a conventional electron cone will provide the adequate distance of about 40 cm between the electron wedge and patient surface for all practical energy ranges. On the patient surface, these narrow electron beams merge to form a smooth tilted intensity profile, as seen in FIG. 2(b). The slope of the profile is controlled by the spacing between the bars and the width of the bars. A concave profile can also be produced if the spatial gradient is symmetric along the midline, for example, as could be achieved with the embodiment shown in FIGS. 7(a) and 7(b).

Electron wedges are advantageous in treating superficial tumors along a curved surface, as well as in electron field matchings.

A second application of this invention relates to the construction of a flattening filter to form a uniform beam profile at an extended distance (e.g., about 3–4 meters from the electron source) with a single direct field for total skin electron therapy (TSE). The current treatment technique for TSE is either a dual-field or triple-field configuration, meaning that two or three fields are used with different angles to form a flattened field at the aforementioned extended distance of about 3–4 meters.

The electron flattening filter of the present invention applies the same principles as the electron wedge filter of the present invention, except that the gradient of the separation between the narrow beams is symmetrical along the central axis of the beam. The purpose of this specific design is to create a concave electron fluence which will compensate the convex Gausian distribution at the extended treatment distance in order to form a flattened profile. Again, the process is iso-energetic.

Figure 3A:
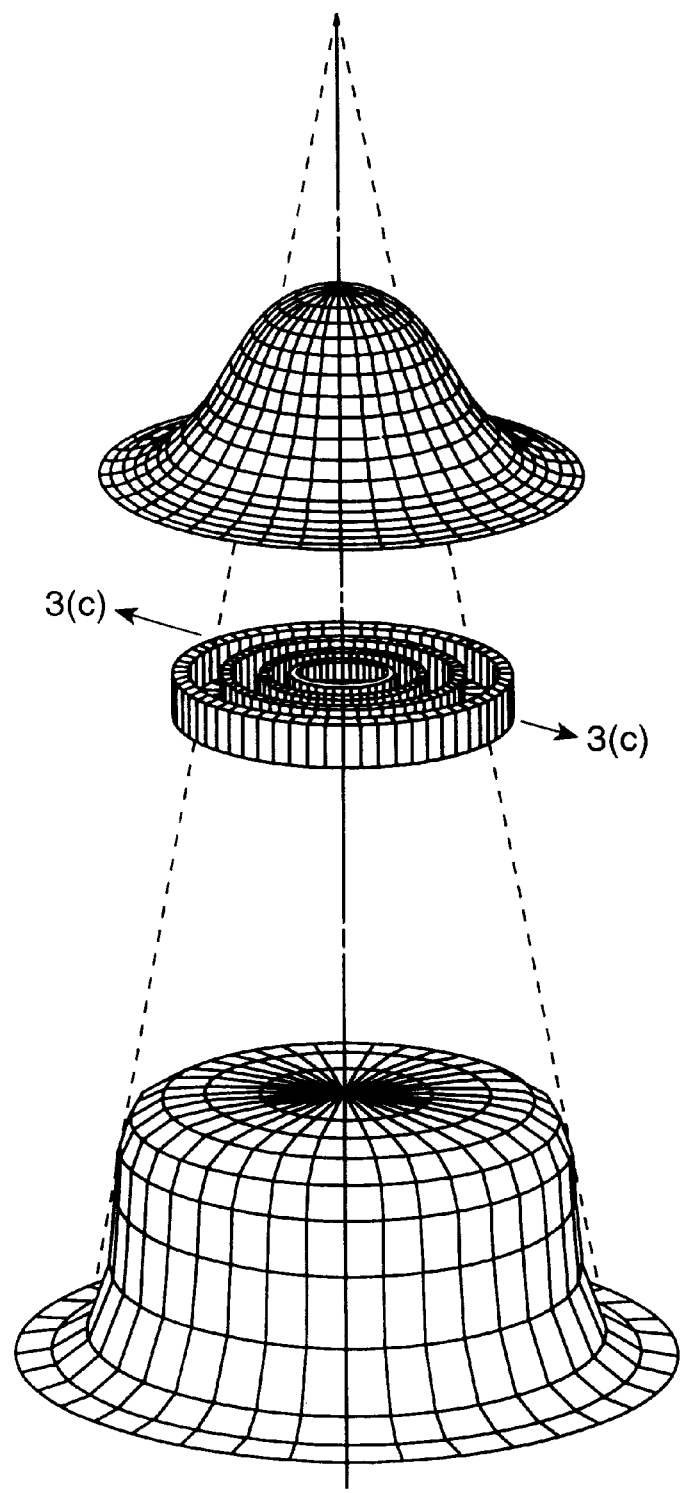
FIGS. 3(a) and 3(b) are perspective views of a concentric ring filter of the present invention.
Figure 7A:
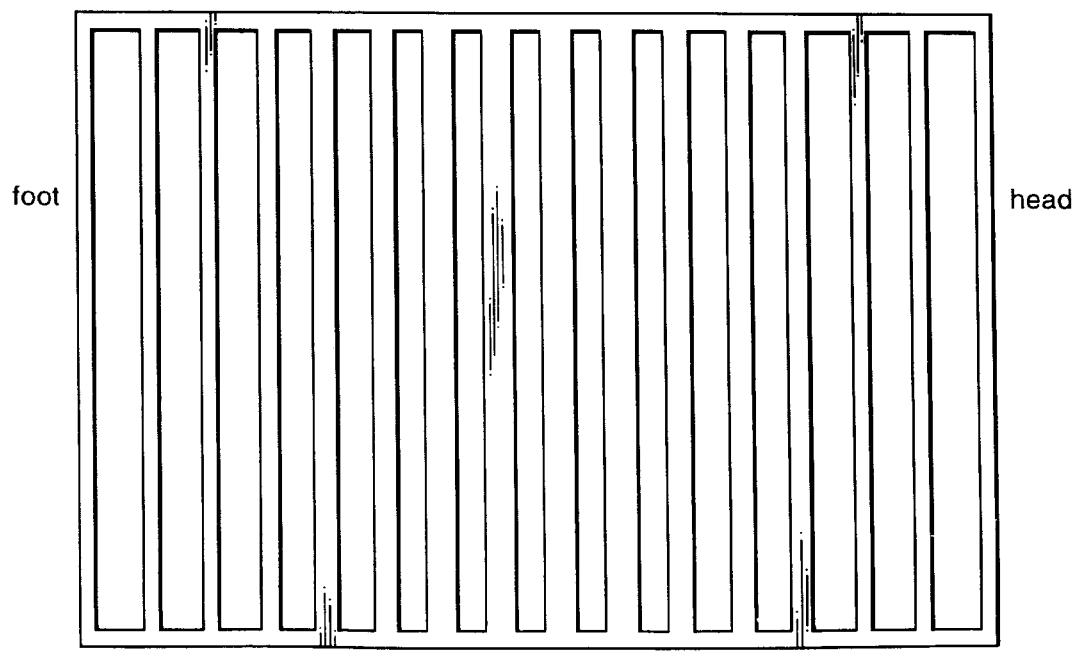
FIG. 7(a) is a plan view.
Figure 7B:
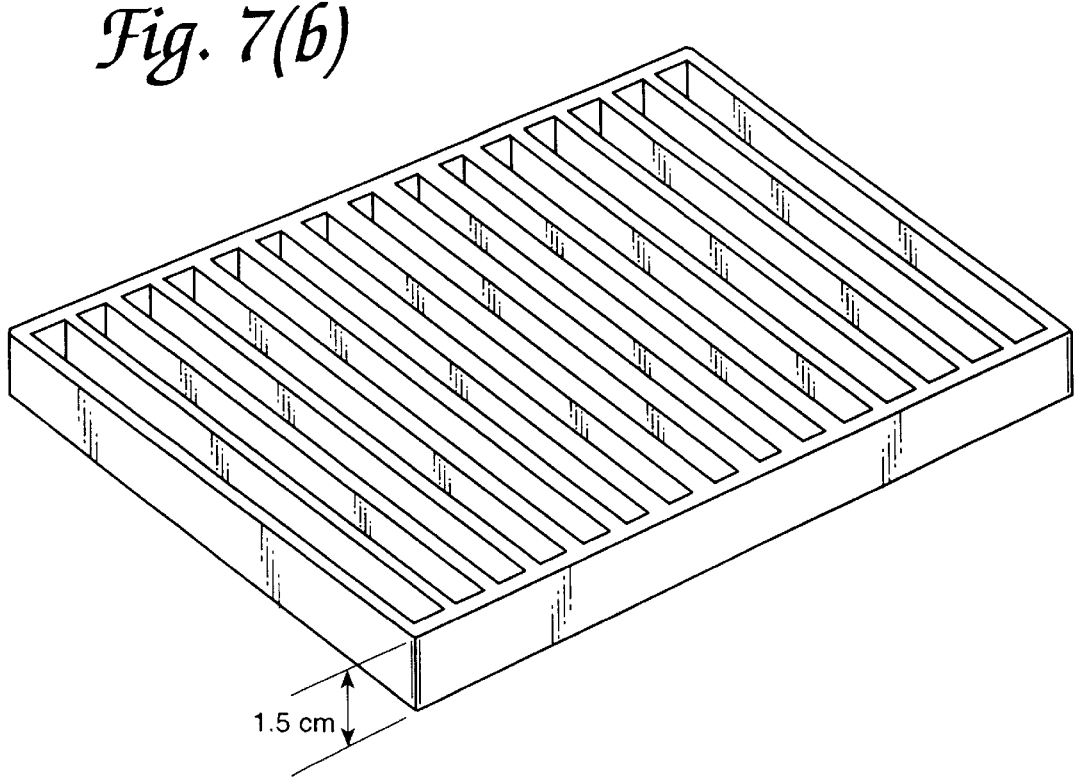
FIG. 7(b) is a perspective view of a flattening filter used for single direct field total skin electron beam treatment. This filter flattens the electron field in one direction (patient's head to foot). When used at standard distance, this filter can be used to produce a concave symmetric profile.
Figure 8:
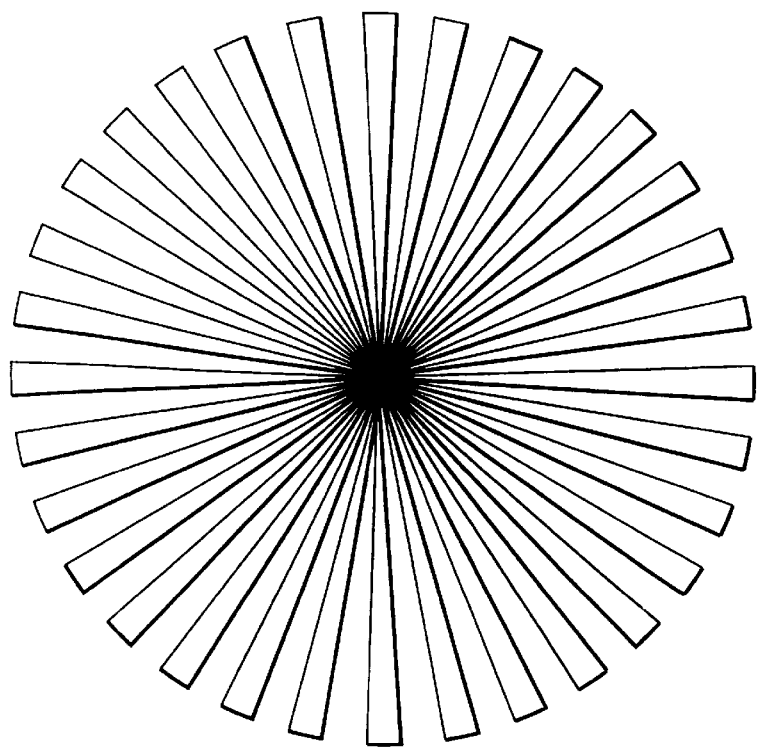
FIG. 8 is a plan view of a star-shaped wedge filter that produces a concave intensity profile similar to that shown in FIG. 3(b).

The arrangement of the attenuator for the TSE filter can be either parallel bars (see FIGS. 7(a) and 7(b)), concentric rings (see FIG. 3(a)), or bars forming a star pattern (see FIG. 8).

The application of this invention can be expanded to the general electron beam flattening filter, intensity modulation for treating other irregularly shaped surfaces instead of using an electron beam bolus.

Electron Wedge Application

Figure 4:
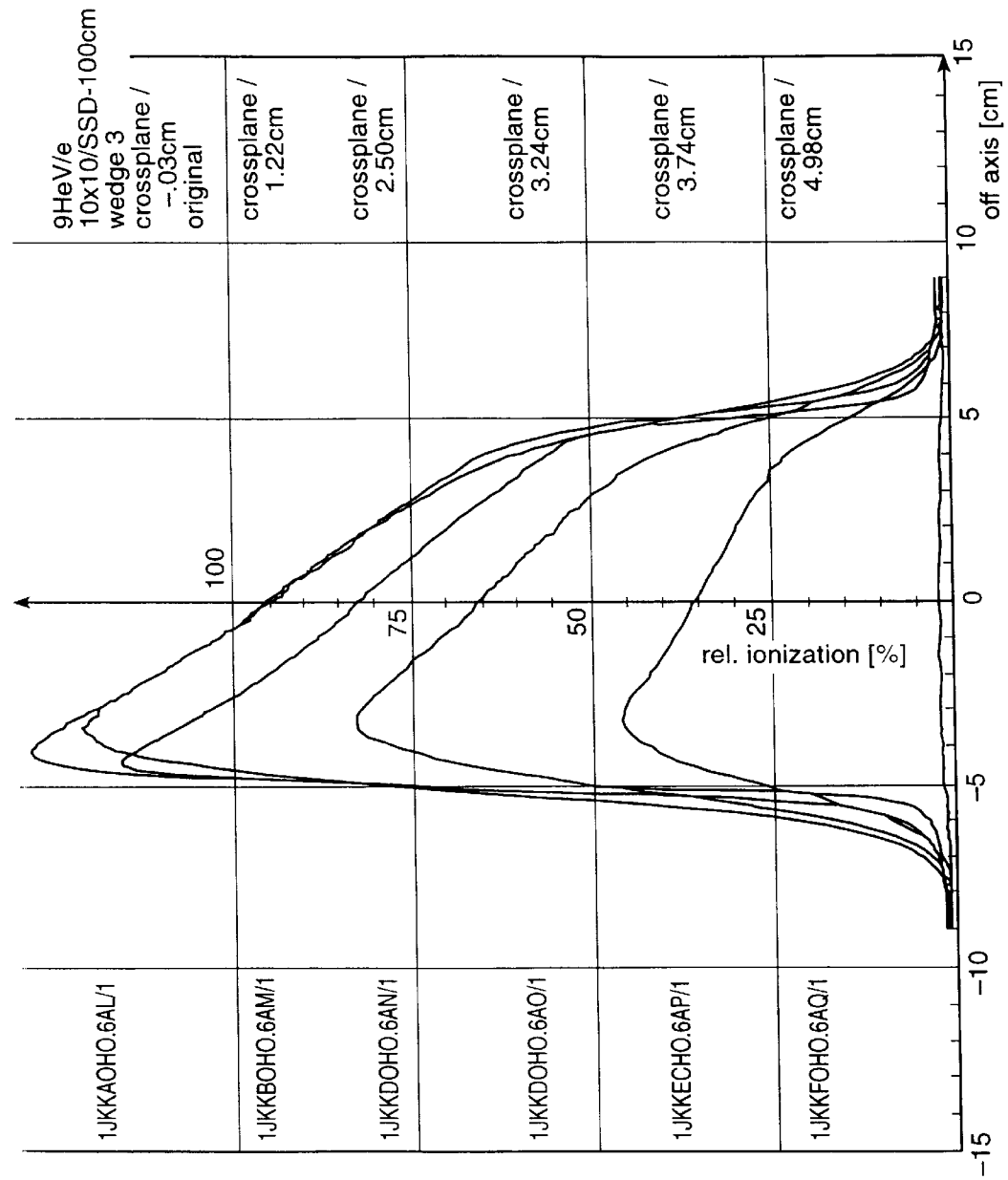
FIG. 4 is a graph of electron beam intensity profiles for a 9 MeV electron beam produced parallel bar wedge filter in accordance with the present invention. The following setup for this is as follows: 10 cm×10 cm cone, 100 cm Source-to-Surface Distance (SSD), and measurements were taken for preprogrammed scanning depths of 0.00 cm, 1.25 cm, 2.50 cm, 3.24 cm, 3.75 cm, and 5.00 cm. Notice that all profiles are parallel to each other, indicating the homogeneity of energy across the field.
Figure 5:
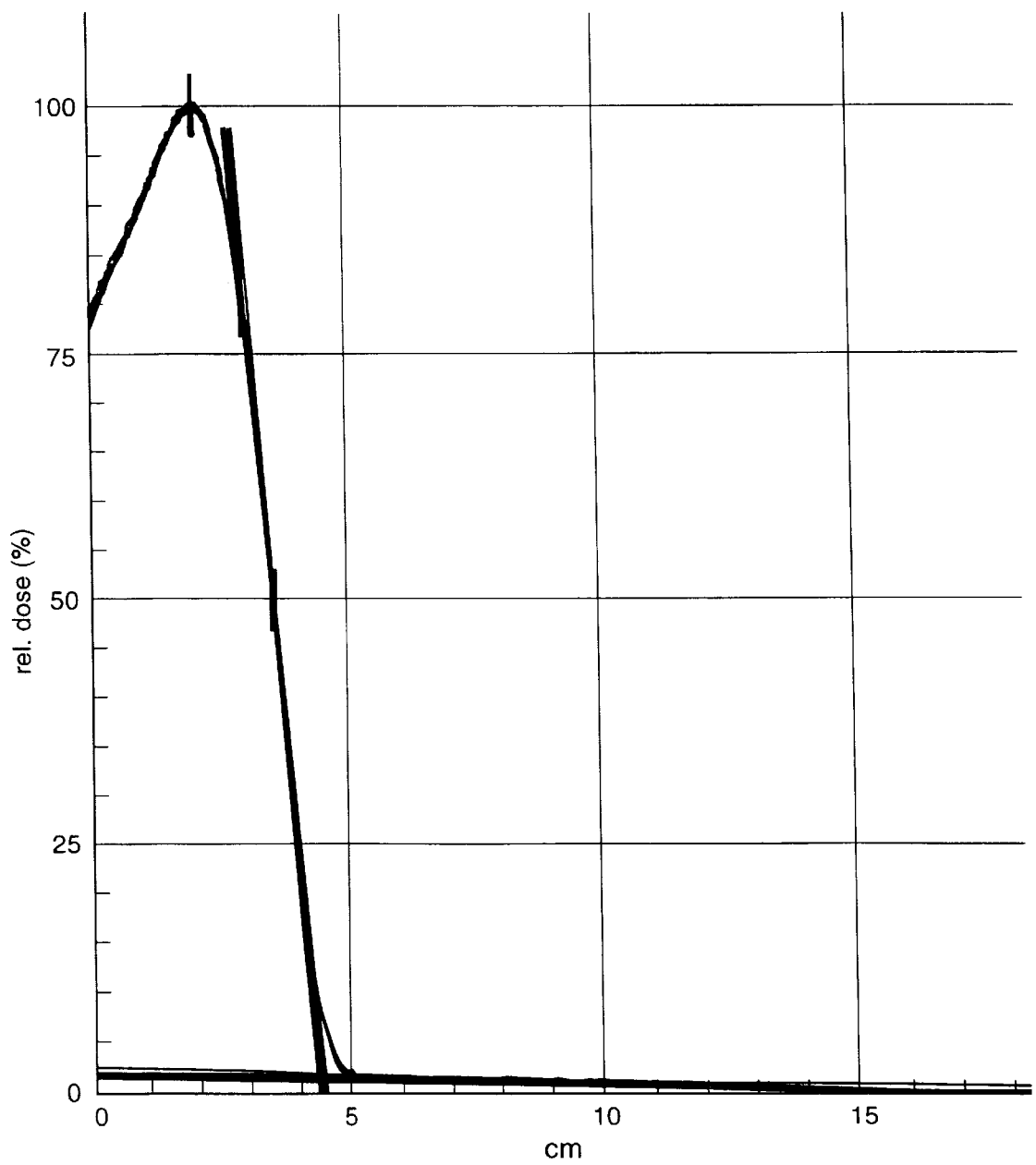
FIG. 5 is a graph which plots a superposition of percentage depth dose curves obtained with open beam and wedge filtered beam (including central axis and off-axis depth dose curves, off-axis depth dose curves were taken at (−1 cm, −1 cm) and at (1 cm, 1 cm)). This plot shows that the electron beam energy remains virtually unchanged before and after wedge filtration.
Figure 6A:
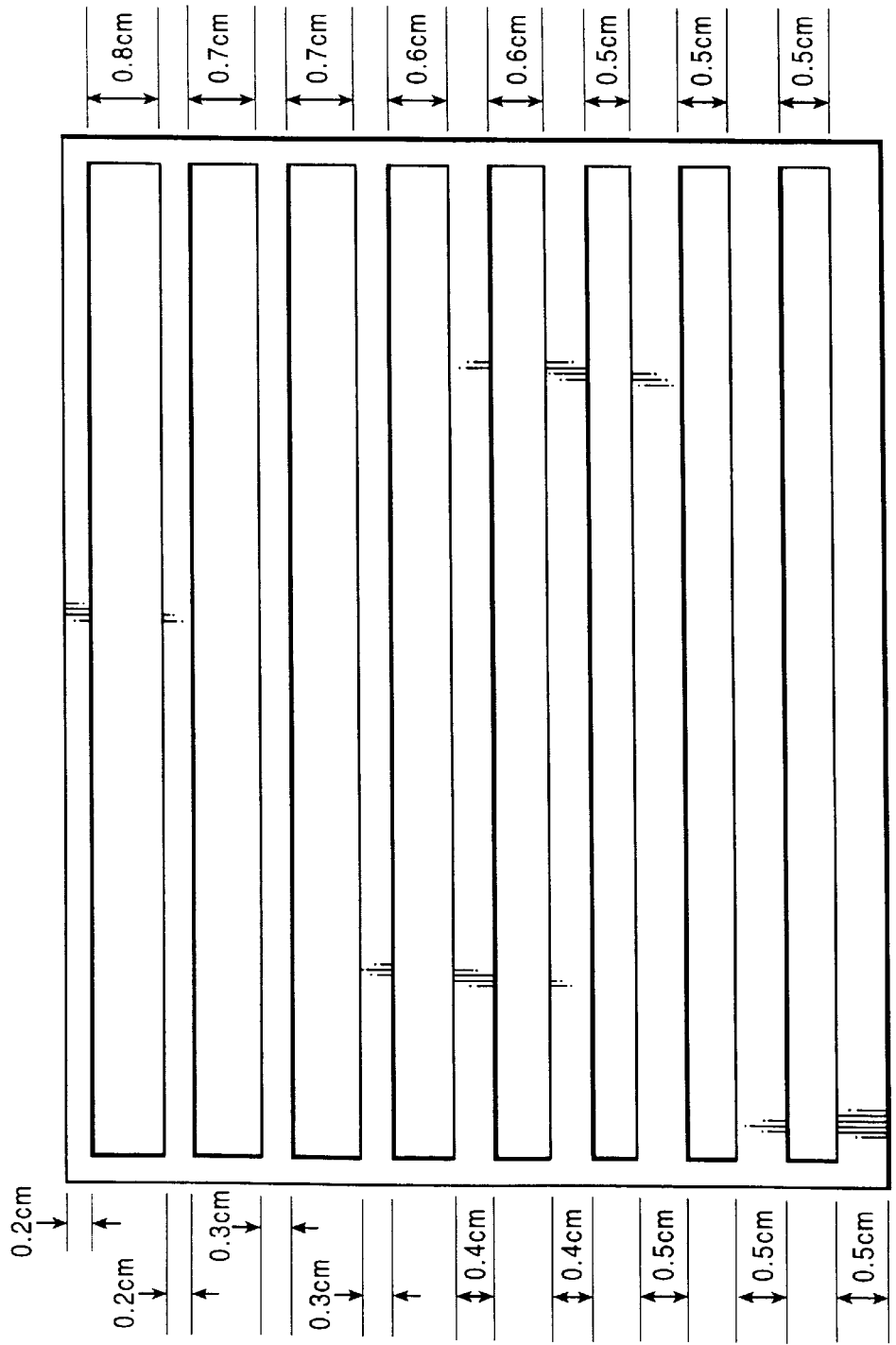
FIG. 6(a) is a plan view.
Figure 6B:
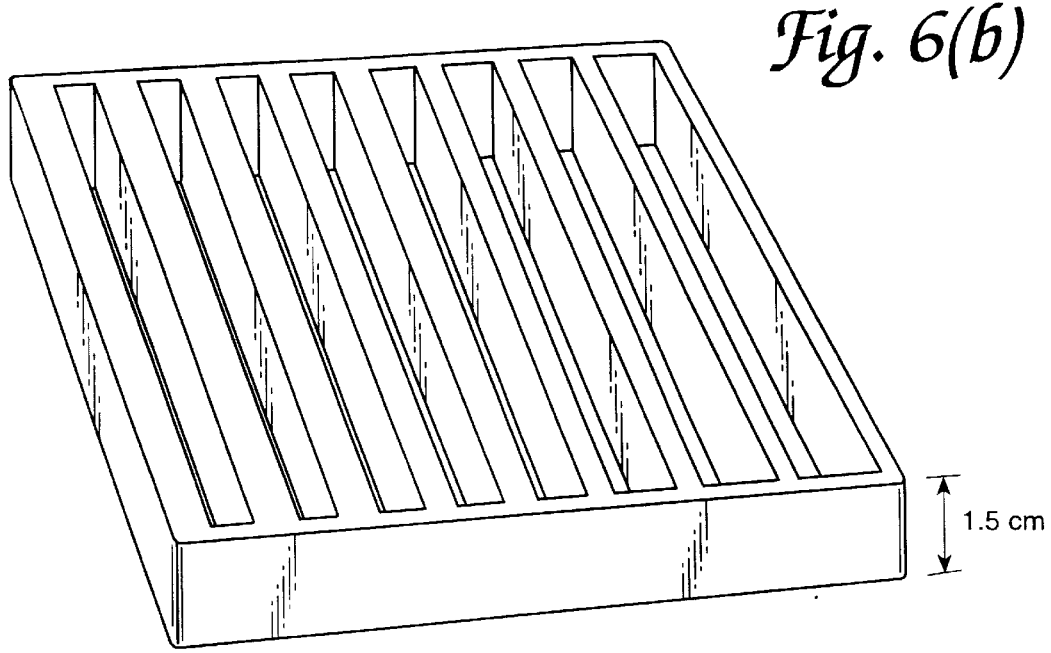
FIG. 6(b) is a perspective view of an electron wedge filter in accordance with the present invention and used to produce the wedge profile shown in FIGS. 4 and 5.

The results shown in FIGS. 4 and 5 were obtained by using the wedge filter shown in FIGS. 6(a) and 6(b). The density and thickness of the metal bars is sufficient to block an electron beam without producing any significant bremsstrahlung contamination, for example, 1.5 cm thickness of cerrobend can be used. Correction of beam divergence can be neglected, especially when higher density metal bars are used (since the thickness can be reduced). The constructed electron wedge is then mounted on a frame which can be inserted into the slot where typical photon wedges or other treatment modules such as TSE modules are usually placed. The electron wedge should be placed above the electron cone, as shown in FIG. 1(b), to produce a smooth tilted profile on the patient surface. The design shown in FIGS. 7(a) and 7(b) can be used at a standard distance to produce a concave intensity profile from a relatively flat intensity profile broad electron beam.

It is contemplated that a multileaf collimator (MLC), which is a computer control system designed and used to form an irregular field shape for photon beam radiation therapy as opposed to the conventional cerrobend block, can be used to provide an electron wedge filter in accordance with the principles of the present invention by using selective leaf openings to form a parallel bar arrangement with designed opening variations. The limitation is that the current MLC can only provide a few discrete opening variation arrangements due to the fact that the location of each leaf is fixed and the width of the leaf is not thin enough to serve this purpose in general.

Figure 10:
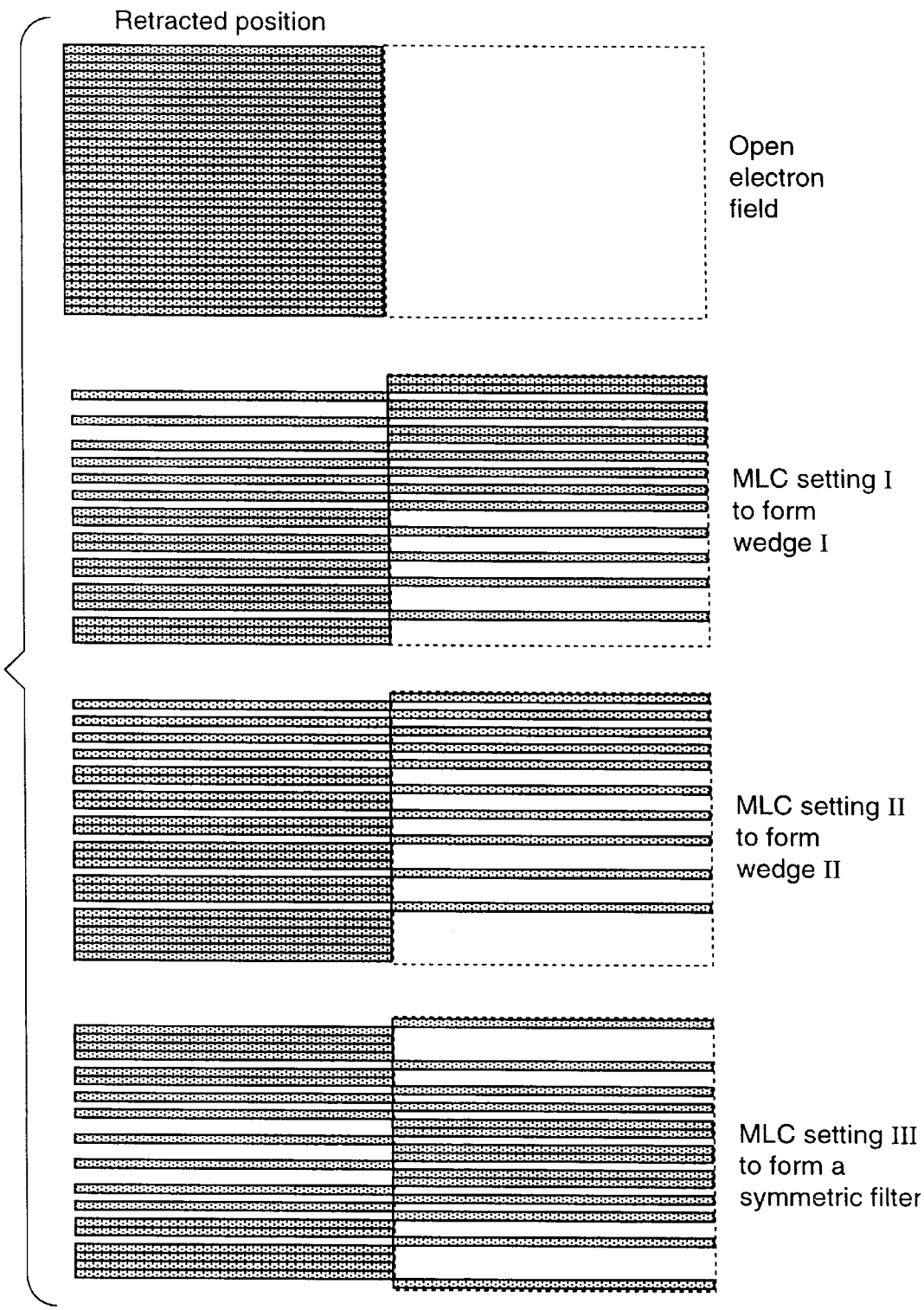
FIG. 10 is an illustration of an embodiment of the invention in which the width and the separation of the parallel bars can be automatically changed by a computer controlled system.

Heretofore, multileaf collimators (MLC) for electron beam intensity modulation with parallel bar arrangement have not been used. Hence, the application of an existing or a modified MLC to form the parallel bar arrangement is also contemplated by this invention to achieve iso-energetic intensity modulation for electron beams. This means that the width and the separation of parallel bars can be automatically changed by a computer controlled system. FIG. 10 illustrates an example of this embodiment of the invention.

Flattening Filter For Total Skin Electron Therapy Application

Since dose uniformity is usually adequate along a patient's width, the flattening filter can be constructed to flatten the dose distribution along the patient's height only. This leads to the wedge configuration shown in FIGS. 7(a) and 7(b). The wedge in FIGS. 7(a) and 7(b) can be mounted to the TSE module frame and the insert the frame to the accessory slot. The spacing between bars should be designed based on the treatment distance (3, 4 or 5 meters).

Figure 9:
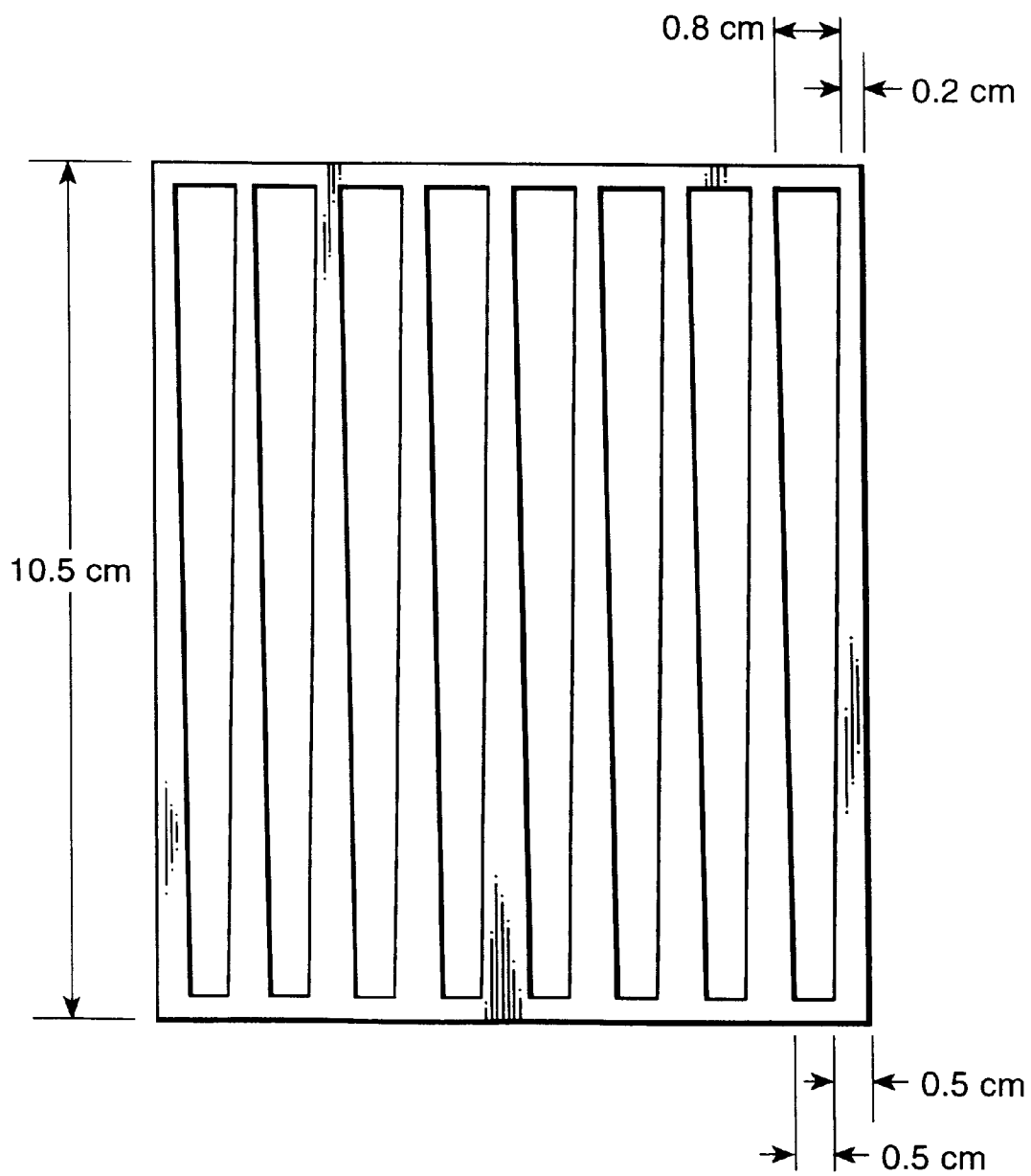
FIG. 9 is a plan view showing a tapered parallel bar configuration for a wedge filter in accordance with another embodiment of the present invention.

A tapered parallel bar configuration shown in FIG. 9 is another design of the present invention which will also serve as an electron beam wedge filter. The difference between FIGS. 6(a), 6(b) and FIG. 9 is the direction of spatial separation gradient. In other words for FIGS. 6(a), 6(b), the intensity gradient is in a direction perpendicular to the bars, while in FIG. 9 the gradient is parallel to the bars.

Figures 3B, 3C:
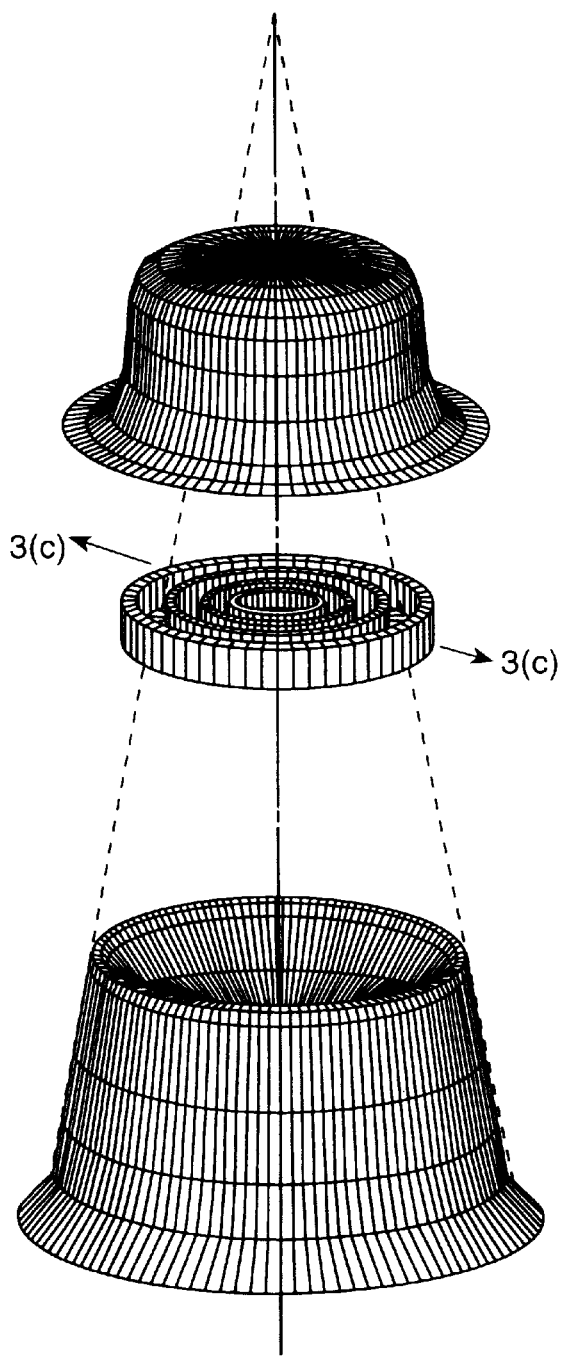
FIG. 3(c) is a cross sectional view of the concentric ring flattening filter taken through the lines 3(c)—3(c) in FIGS. 3(a) and 3(b), and shows the progressively increased spacing between rings as the radial distance from the center of the flattening filter increases.

A filter with a concentric ring configuration can be built with different sizes, and can be used in the head of an accelerator below the scattering foil to flatten the beam at normal distance (100 cm) as shown in FIG. 3(a), or be used to modify a flattened beam profile into a concave profile at normal distance (100 cm), as shown in FIG. 3(b). The concentric ring configuration can also be used to produce a flattened beam at an extended distance (3–4 m) for total skin treatment.

In an alternate embodiment, it is contemplated that an alternate concentric ring configuration can be used to convert a flat electron beam intensity profile into a convex intensity profile. In this embodiment, the spacing between the rings is wider at the center portions of the filter than at the peripheral regions (compare this to FIG. 3(a)).

A star shaped configuration can produce an effect similar to that for the concentric ring configuration. In other words, it can be use to convert an incoming convex dome shaped intensity beam into a flattened beam, or convert an incoming flattened beam into a concave beam. FIG. 8 demonstrates this star shaped design.

Conclusion

While the use of electron beams is a widely used modality for radiation cancer treatment, the present invention provides a general technique which can be used to modulate the intensity of a static electron field without changing the electron beam energy. Typical intensity modulations are used to produce tilted wedge beam profiles and flattened beam profiles. Although the electron beam can be filtered through a wedge shape absorber to produce a tilted intensity profile (which is the technique used in x-ray or gamma ray therapy), the serious beam energy degradation by the absorber makes this design undesirable for electron beams. The present invention utilizes the Coulomb multiple-scattering principle to produce a tilted or flattened intensity profile by merging multiple narrow slit electron beams. Using this method, the energy of the electron beam remains substantially unchanged, hence the modulation is substantially iso-energetic.

The present invention is advantageous in that it can be used to produce (1) a static tilted wedge, concave, or other shape electron beam profile without degrading the beam energy across the whole field, (2) a static flattened electron beam at extended treatment distance without degrading the beam energy across the whole field. In addition, the internal scattering/flattening electron foil/filter can be designed based on the proposed concentric ring configuration to improve the electron beam energy spectrum. Although only the preferred embodiments have been described in detail above, those skilled in the art will readily appreciate that many modifications of the exemplary embodiments are possible in without materially parting from the novel teachings and advantages of this invention.

What is claimed is:

1. An iso-energetic intensity modulating filter for a charged-particle beam comprising:

a plurality of attenuating members arranged to define a plurality of transparent regions that are substantially transparent to a charged-particle beam, wherein said plurality of attenuating members each have a thickness in a direction of travel of said charged-particle beam and are constructed from a material with a density sufficient in combination with said thickness to block said charged-particle beam free from a significant production of bremsstrahlung contamination of an intensity modulated charged-particle beam, and wherein when said charged-particle beam passes through said intensity modulating filter an intensity profile of said charged-particle beam is modified without substantially modifying an energy spectrum of said charged-particle beam, hence, said intensity modulating filter is iso-energetic.

2. An iso-energetic intensity modulating filter according to claim 1, wherein said material of said plurality of attenuating members is selected from a group consisting of lead, tungsten, copper, cerrobend, steel and iron, and said charged-particle beam is an electron beam.

3. An iso-energetic intensity modulating filter according to claim 2, wherein said material of said plurality of attenuating members is selected from a group consisting of lead and tungsten, and said thickness of said plurality of attenuating members is about 1.5 cm.

4. An iso-energetic intensity modulating filter according to claim 1, wherein said plurality of attenuating members form a wedge filter.

5. An iso-energetic intensity modulating filter according to claim 4, wherein said plurality of attenuating members are constructed and arranged to form a para-bar wedge filter, said plurality of attenuating members of said para-bar wedge filter includes a plurality of parallel bars, each of said parallel bars having a longitudinal axis and a rectangular cross-sectional shape along a cross-sectional cut perpendicular to said longitudinal axis, said rectangular cross-sectional shape of each of said plurality of parallel bars being substantially uniform along said longitudinal axis of each of said parallel bars, each said longitudinal axis being substantially parallel to all other said longitudinal axes of said plurality of parallel bars, each of said plurality of transparent regions having a width in a direction along a transverse line that is substantially orthogonal to each longitudinal axis of said plurality of parallel bars, and said widths of said plurality of transparent regions defining a width gradient of said transparent regions along said transverse line that is nonzero.

6. An iso-energetic intensity modulating filter according to claim 4, wherein said plurality of attenuating members are constructed and arranged to form a tapered-bar wedge filter, said plurality of attenuating members of said tapered-bar wedge filter includes a plurality of tapered bars, each of said tapered bars having a longitudinal axis and a rectangular cross-sectional shape along a cross-sectional cut perpendicular to said longitudinal axis, said rectangular cross-sectional shape of each of said plurality of tapered bars varying along said longitudinal axis of each of said tapered bars, each said longitudinal axis being substantially parallel to all other said longitudinal axes of said plurality of tapered bars, each of said plurality of transparent regions having a plurality of widths in directions along transverse lines that are substantially orthogonal to each longitudinal axis of said plurality of tapered bars, and said plurality of widths of each of said plurality of transparent regions defining a width gradient of said transparent region along a direction substantially parallel to said plurality of longitudinal axes, said width gradient of each of said plurality of transparent regions being nonzero.

7. An iso-energetic intensity modulating filter according to claim 4, wherein said plurality of attenuating members are constructed and arranged to form a para-bar flattening filter, said plurality of attenuating members of said para-bar flattening filter including a plurality of parallel bars, each of said parallel bars having a longitudinal axis and a rectangular cross-sectional shape along a cross-sectional cut perpendicular to said longitudinal axis, said rectangular cross-sectional shape of each of said plurality of parallel bars being substantially uniform along said longitudinal axis of each of said parallel bars, each said longitudinal axis being substantially parallel to all other said longitudinal axes of said plurality of parallel bars, each of said plurality of transparent regions having a width in a direction along a transverse line that is substantially orthogonal to each longitudinal axis of said plurality of parallel bars, and said widths of said plurality of transparent regions defining a first width gradient of said transparent regions along said transverse line that is nonzero, and a second width gradient of said transparent regions along said transverse line that is nonzero, said first width gradient being opposite in sign to said second width gradient.

8. An iso-energetic intensity modulating filter according to claim 4, wherein said plurality of attenuating members are constructed and arranged to form a ring flattening filter, said plurality of attenuating members of said ring flattening filter including a plurality of substantially concentric rings disposed such that said plurality of transparent regions have a nonzero width gradient along a radial direction of said substantially concentric rings.

9. An iso-energetic intensity modulating filter according to claim 4, wherein said plurality of attenuating members are constructed and arranged to form a star-shaped flattening filter, said plurality of attenuating members of said star-shaped flattening filter including a plurality of wedge sections that are substantially in shapes of wedge sections of a disk disposed such that said plurality of transparent regions have a nonzero width gradient of circumferential widths along a radial direction of said star-shaped flattening filter.

10. An iso-energetic intensity modulating filter according to claim 4, wherein said plurality of attenuating members are constructed and arranged to form a para-bar concave filter, said plurality of attenuating members of said para-bar concave filter includes a plurality of parallel bars, each of said parallel bars having a longitudinal axis and a rectangular cross-sectional shape along a cross-sectional cut perpendicular to said longitudinal axis, said rectangular cross-sectional shape of each of said plurality of parallel bars being substantially uniform along said longitudinal axis of each of said parallel bars, each said longitudinal axis being substantially parallel to all other said longitudinal axes of said plurality of parallel bars, each of said plurality of transparent regions having a width in a direction along a transverse line that is substantially orthogonal to each longitudinal axis of said plurality of parallel bars, and said widths of said plurality of transparent regions defining a first width gradient of said transparent regions along said transverse line that is nonzero, and a second width gradient of said transparent regions along said transverse line that is nonzero, said first width gradient being opposite in sign to said second width gradient, said first and second width gradients having a value such that said intensity modulated charged particle beam has an intensity profile that is concave in a center of said intensity profile.

11. An iso-energetic intensity modulating filter according to claim 4, wherein said plurality of attenuating members are constructed and arranged to form a ring concave filter, said plurality of attenuating members of said ring concave filter including a plurality of substantially concentric rings disposed such that said plurality of transparent regions have a nonzero width gradient along a radial direction of said substantially concentric rings, and said gradient having a value such that said intensity modulated charged particle beam has an intensity profile that is concave in a center of said intensity profile.

12. An iso-energetic intensity modulating filter according to claim 1, wherein said plurality of attenuating members are movably disposed such that a movement of at least one of said plurality of attenuating members changes a size of at least one of said plurality of transparent regions.

13. An iso-energetic intensity modulating filter according to claim 1, wherein each attenuating member of said plurality of attenuating members has a width in a direction transverse to said direction of travel of said charged-particle beam and a separation from each other attenuating member, said widths of said plurality of attenuating members, and said separations of said plurality of attenuating members result in intensity modulation of said charged-particle beam.

14. An iso-energetic intensity modulating filter according to claim 1, wherein said plurality of attenuating members form a flattening filter.

15. An iso-energetic intensity modulating filter according to claim 1, wherein said plurality of attenuating members form a concave filter.

16. An iso-energetic intensity modulating filter according to claim 1, wherein said charged-particle beam is an electron beam.

17. An iso-energetic intensity modulating filter according to claim 16, wherein said electron beam consists of a plurality of electrons having an average energy within the range from 6 MeV to 20 MeV, inclusive.

18. An iso-energetic intensity modulating filter according to claim 17, wherein said thickness of said plurality of attenuating members is about 1.5 cm and said plurality of attenuating members are made from a material selected from the group of materials consisting of lead, tungsten, cerrobend, copper, steel and iron.

19. An iso-energetic intensity adjustable charged-particle beam therapeutic device, comprising:

an accelerator that produces a charged-particle beam;

an iso-energetic intensity modulating filter for said charged-particle beam disposed in a path of said charged-particle beam, wherein said iso-energetic intensity modulating filter has a plurality of attenuating members arranged to define a plurality of regions that are substantially transparent to said beam of charged-particles, said plurality of attenuating members each have a thickness in a direction of travel of said beam of charged-particles and are constructed from a material with a density sufficient in combination with said thickness to block said beam of charged-particles free from a significant production of bremsstrahlung contamination of an intensity modulated charged-particle beam, and wherein when said charged-particle beam passes through said intensity modulating filter an intensity profile of said charged-particle beam is modified without substantially modifying an energy spectrum of said charged-particle beam, hence, said intensity modulating filter is iso-energetic.

20. An iso-energetic intensity adjustable charged-particle beam therapeutic device according to claim 19, wherein said plurality of attenuating members are constructed and arranged to form one of a wedge filter, a flattening filter, and a concave filter.

21. An iso-energetic intensity adjustable charged-particle beam therapeutic device according to claim 19, wherein said beam of charged particles is a beam of electrons.

22. An iso-energetic intensity adjustable charged-particle beam therapeutic device according to claim 21, wherein said electron beam consists of a plurality of electrons having an average energy within the range from 6 MeV to 20 MeV, inclusive.

23. An iso-energetic intensity adjustable charged-particle beam therapeutic device according to claim 22, wherein said thickness of said plurality of attenuating members is about 1.5 cm and said plurality of attenuating members are made from a material selected from the group of materials consisting of lead, tungsten, cerrobend, copper, steel and iron.

24. An iso-energetic intensity modulating method for a charged-particle beam, comprising:

attenuating a first plurality of portions of said charged-particle beam; and permitting a second plurality of portions of said charged-particle beam to pass substantially free from attenuation, wherein said attenuating of said first plurality of portions of said charged-particle beam attenuates said first plurality of portions substantially free from a production of bremsstrahlung contamination of an intensity modulated charged-particle beam, and wherein when said charged-particle beam passes through said intensity modulating filter an intensity profile of said charged-particle beam is modified without substantially modifying an energy spectrum of said charged-particle beam, hence, said intensity modulating filter is iso-energetic.

25. An improved iso-energetic intensity-modulated charged-particle beam produced by filtering a charged-particle beam according to the method of claim 24.

26. A method of medical treatment, comprising:

arranging a treatment region of a patient's body such that said treatment region is proximate to a source of a charged-particle beam;

disposing an iso-energetic intensity modulating filter for said charged-particle beam between said source of said charged-particle beam and said treatment region of said patient's body;

directing said charged-particle beam from said charged-particle beam source such that it is incident upon said iso-energetic intensity modulating filter; and directing an intensity modulated charged-particle beam that is an output beam from said iso-energetic intensity modulating filter such that it is incident upon said treatment region of said patient's body, wherein when said charged-particle beam passes through said intensity modulating filter an intensity profile of said charged-particle beam is modified without substantially modifying an energy spectrum of said charged-particle beam, hence, said intensity modulating filter is iso-energetic.

27. A method of medical treatment according to claim 26, wherein said charged particle beam is an electron beam.

28. A method of medical treatment according to claim 27, wherein said electron beam consists of a plurality of electrons having an average energy within the range from 6 MeV to 20 MeV, inclusive.

29. A method of medical treatment according to claim 28, wherein said thickness of said plurality of attenuating members is about 1.5 cm and said plurality of attenuating members are made from a material selected from the group of materials consisting of lead, tungsten, cerrobend, copper, steel and iron.

* * * * *